(12) United States Patent
Nakamura

(10) Patent No.: US 11,627,918 B2
(45) Date of Patent: Apr. 18, 2023

(54) STATE EXTRAPOLATION DEVICE, STATE EXTRAPOLATION PROGRAM, AND STATE EXTRAPOLATION METHOD

(71) Applicant: CLARION CO., LTD., Saitama (JP)

(72) Inventor: Tomohiro Nakamura, Saitama (JP)

(73) Assignee: CLARION CO., LTD., Saitama (JP)

( * ) Notice: Subject to any disclaimer, the term of this patent is extended or adjusted under 35 U.S.C. 154(b) by 306 days.

(21) Appl. No.: 17/004,809

(22) Filed: Aug. 27, 2020

(65) Prior Publication Data

US 2021/0059615 A1  Mar. 4, 2021

(30) Foreign Application Priority Data

Aug. 27, 2019  (JP) .............................. JP2019-154470

(51) Int. Cl.
*A61B 5/00* (2006.01)
*G16H 40/67* (2018.01)
(Continued)

(52) U.S. Cl.
CPC ............ *A61B 5/7282* (2013.01); *A61B 5/024* (2013.01); *A61B 5/165* (2013.01); *A61B 5/18* (2013.01);
(Continued)

(58) Field of Classification Search
CPC ....... A61B 5/7282; A61B 5/024; A61B 5/165; A61B 5/18; A61B 5/4094; A61B 5/7267; A61B 5/7475; A61B 5/742; G16H 40/67; G16H 50/30; G06N 20/00; B60W 40/08; B60W 50/14; B60W 2540/229; B60W 2540/221; B60W 2040/0827; G06V 20/597; G06V 40/16
See application file for complete search history.

(56) References Cited

U.S. PATENT DOCUMENTS 8,340,902 B1 * 12/2012 Chiang ................ G05D 1/0044
                                                          382/104
9,549,702 B1 * 1/2017 Kerness ............... A61B 5/4845
(Continued)

FOREIGN PATENT DOCUMENTS

JP  2015-226696 A  12/2015
JP  2018-127112 A  8/2018
WO  2017/105976 A1  6/2017

OTHER PUBLICATIONS

Li et al., A multimodal psychological physiological and behavioural dataset for human emotions in driving tasks (Year: 2022).*
(Continued)

*Primary Examiner* — Quang Pham
(74) *Attorney, Agent, or Firm* — Volpe Koenig

(57) ABSTRACT

An object of the present invention is to more appropriately extrapolate a sign of a state that may affect a movement of a user. A state extrapolation device according to the present invention includes a vital sign acquisition unit that acquires a vital sign of a user, and a sign detection unit that uses a learned model that has learned, as training data, sign data about the vital sign related to a predetermined physical condition abnormality, and detects a sign by determining whether or not the vital sign of the user corresponds to a sign of the predetermined physical condition abnormality.

11 Claims, 15 Drawing Sheets

(51) Int. Cl.
| | |
|---|---|
| *G16H 50/30* | (2018.01) |
| *G06N 20/00* | (2019.01) |
| *A61B 5/024* | (2006.01) |
| *A61B 5/16* | (2006.01) |
| *A61B 5/18* | (2006.01) |
| *B60W 40/08* | (2012.01) |
| *B60W 50/14* | (2020.01) |
| *G06V 20/59* | (2022.01) |
| *G06V 40/16* | (2022.01) |

(52) U.S. Cl.
CPC .......... *A61B 5/4094* (2013.01); *A61B 5/7267* (2013.01); *A61B 5/7475* (2013.01); *B60W 40/08* (2013.01); *B60W 50/14* (2013.01); *G06N 20/00* (2019.01); *G16H 40/67* (2018.01); *G16H 50/30* (2018.01); *A61B 5/742* (2013.01); *B60W 2040/0827* (2013.01); *B60W 2540/221* (2020.02); *B60W 2540/229* (2020.02); *G06V 20/597* (2022.01); *G06V 40/16* (2022.01)

(56) References Cited

U.S. PATENT DOCUMENTS

| | | | | |
|---|---|---|---|---|
| 9,809,228 | B2* | 11/2017 | Hong | B60W 50/14 |
| 9,870,689 | B1* | 1/2018 | Deluca | G04G 13/02 |
| 10,231,660 | B2* | 3/2019 | Kojima | G08B 21/06 |
| 10,235,859 | B1* | 3/2019 | Hiles | A61B 5/18 |
| 10,384,602 | B1* | 8/2019 | Csabi | B60Q 9/008 |
| 11,040,720 | B2* | 6/2021 | Satou | B60W 40/02 |
| 2005/0177051 | A1* | 8/2005 | Almen | A61B 5/02438 |
| | | | | 600/509 |
| 2006/0200008 | A1* | 9/2006 | Moore-Ede | B60K 28/06 |
| | | | | 128/920 |
| 2008/0231703 | A1* | 9/2008 | Nagata | H04N 7/181 |
| | | | | 348/E7.086 |
| 2009/0147996 | A1* | 6/2009 | Peng | G01S 11/12 |
| | | | | 382/106 |
| 2009/0174560 | A1* | 7/2009 | Ahmad | A61B 5/6887 |
| | | | | 340/576 |
| 2013/0009761 | A1* | 1/2013 | Horseman | A61B 5/6893 |
| | | | | 340/576 |
| 2013/0093603 | A1* | 4/2013 | Tschirhart | A61B 5/18 |
| | | | | 340/902 |
| 2013/0167207 | A1* | 6/2013 | Davis | G06F 21/316 |
| | | | | 726/5 |
| 2013/0212230 | A1* | 8/2013 | Morinaga | G06Q 30/0241 |
| | | | | 709/219 |
| 2014/0059066 | A1* | 2/2014 | Koloskov | G06F 16/40 |
| | | | | 361/679.01 |
| 2014/0111647 | A1* | 4/2014 | Atsmon | G06F 16/29 |
| | | | | 348/148 |
| 2014/0335814 | A1* | 11/2014 | Gudlavenkatasiva | H04W 76/50 |
| | | | | 455/404.1 |
| 2015/0022338 | A1* | 1/2015 | Hwang | G08B 5/222 |
| | | | | 340/501 |
| 2015/0025917 | A1* | 1/2015 | Stempora | G02B 27/0093 |
| | | | | 705/4 |
| 2015/0065082 | A1* | 3/2015 | Sehgal | G08B 25/016 |
| | | | | 455/404.2 |
| 2015/0127570 | A1* | 5/2015 | Doughty | G06Q 50/265 |
| | | | | 705/325 |
| 2015/0254955 | A1* | 9/2015 | Fields | G06Q 30/0283 |
| | | | | 340/576 |
| 2015/0324698 | A1* | 11/2015 | Karaoguz | H04L 67/12 |
| | | | | 706/46 |
| 2015/0328985 | A1* | 11/2015 | Kim | B60W 50/16 |
| | | | | 180/272 |
| 2015/0351681 | A1* | 12/2015 | Lee | G08B 21/06 |
| | | | | 600/595 |
| 2016/0001781 | A1* | 1/2016 | Fung | G06K 9/00536 |
| | | | | 701/36 |
| 2016/0029940 | A1* | 2/2016 | Iizuka | B60K 28/00 |
| | | | | 701/23 |
| 2016/0050270 | A1* | 2/2016 | Kadoda | H04L 67/1095 |
| | | | | 709/217 |
| 2016/0071393 | A1* | 3/2016 | Kaplan | A61B 5/162 |
| | | | | 340/539.12 |
| 2016/0151603 | A1* | 6/2016 | Shouldice | G16H 20/30 |
| | | | | 600/26 |
| 2016/0192879 | A1* | 7/2016 | Yamashita | A61B 5/721 |
| | | | | 600/407 |
| 2016/0275798 | A1* | 9/2016 | Maytal | G08B 21/187 |
| 2016/0297431 | A1* | 10/2016 | Eigel | B60W 30/06 |
| 2016/0318395 | A1* | 11/2016 | Cofer | G08B 25/08 |
| 2017/0003666 | A1* | 1/2017 | Nunn | A47C 27/083 |
| 2017/0035212 | A1* | 2/2017 | Erko | A47C 27/083 |
| 2017/0086732 | A1* | 3/2017 | Tribble | A61B 5/746 |
| 2017/0106858 | A1* | 4/2017 | Li | G08B 21/06 |
| 2017/0112391 | A1* | 4/2017 | Stivoric | A61B 5/0022 |
| 2017/0136203 | A1* | 5/2017 | Swain | A61M 16/109 |
| 2017/0172520 | A1* | 6/2017 | Kannan | A61B 5/6801 |
| 2017/0263109 | A1* | 9/2017 | Kim | G05B 23/02 |
| 2017/0300655 | A1* | 10/2017 | Lane | G16H 10/60 |
| 2017/0316685 | A1* | 11/2017 | Yun | G08G 1/096716 |
| 2017/0331954 | A1* | 11/2017 | Kotnis | H04L 51/52 |
| 2017/0355377 | A1* | 12/2017 | Vijaya Kumar | B60W 50/0098 |
| 2017/0365165 | A1* | 12/2017 | Landfors | B60W 40/09 |
| 2018/0012085 | A1* | 1/2018 | Blayvas | H04N 13/20 |
| 2018/0093672 | A1* | 4/2018 | Terwilliger | G08B 21/06 |
| 2018/0105180 | A1* | 4/2018 | Fung | A61B 5/1122 |
| 2018/0116415 | A1* | 5/2018 | Karschnik | A61B 5/4809 |
| 2018/0126901 | A1* | 5/2018 | Levkova | B60W 40/09 |
| 2018/0144714 | A1* | 5/2018 | Khorasani | G09G 5/02 |
| 2018/0146354 | A1* | 5/2018 | Patel | H04W 4/90 |
| 2018/0174457 | A1* | 6/2018 | Taylor | G08G 1/096741 |
| 2018/0244288 | A1* | 8/2018 | Glaser | B60W 50/14 |
| 2018/0312164 | A1* | 11/2018 | Sasabuchi | B60W 30/18018 |
| 2018/0338733 | A1* | 11/2018 | Jain | A61B 5/6802 |
| 2018/0358113 | A1* | 12/2018 | Cronin | G06F 21/32 |
| 2018/0365998 | A1* | 12/2018 | Shibata | G08G 1/096791 |
| 2019/0008450 | A1* | 1/2019 | Gurievsky | A61B 5/4812 |
| 2019/0038204 | A1* | 2/2019 | Beck | A61B 5/024 |
| 2019/0056732 | A1* | 2/2019 | Aoi | B60W 40/08 |
| 2019/0064805 | A1* | 2/2019 | Frazzoli | G05D 1/0246 |
| 2019/0070386 | A1* | 3/2019 | Raut | A61B 5/4812 |
| 2019/0082044 | A1* | 3/2019 | Melendez | H04W 4/023 |
| 2019/0092337 | A1* | 3/2019 | Chua | B60W 30/14 |
| 2019/0100216 | A1* | 4/2019 | Volos | G06Q 40/08 |
| 2019/0122525 | A1* | 4/2019 | Lancelle | B60Q 9/00 |
| 2019/0130719 | A1* | 5/2019 | D'Amico | G08B 21/02 |
| 2019/0152492 | A1* | 5/2019 | el Kaliouby | G06K 9/6273 |
| 2019/0180283 | A1* | 6/2019 | Unnerstall | G06Q 20/4016 |
| 2019/0298230 | A1* | 10/2019 | Nicholson | A61B 5/14532 |
| 2019/0315369 | A1* | 10/2019 | Thompson | B60W 60/00 |
| 2020/0015058 | A1* | 1/2020 | Wu | H04L 67/306 |
| 2020/0020165 | A1* | 1/2020 | Tran | G06N 20/10 |
| 2020/0094737 | A1* | 3/2020 | Furukawa | B60W 50/08 |
| 2020/0196920 | A1* | 6/2020 | Vaddiraju | A61B 5/14532 |
| 2020/0330017 | A1* | 10/2020 | Irwin | A61B 5/25 |
| 2022/0067412 | A1* | 3/2022 | Takamoto | A61B 5/18 |
| 2022/0118985 | A1* | 4/2022 | Austin | G06N 20/00 |
| 2022/0277570 | A1* | 9/2022 | Takamoto | A61B 5/18 |

OTHER PUBLICATIONS

Qu et al., Predictive Model and Analysis of Psychological Depression Based on College Students' Behavior Data Mining (Year: 2022).*

Yang et al., Measuring and Improving User Experience Through Artificial Intelligence-Aided Design (Year: 2020).*

Extended European Search Report dated Jan. 22, 2021 for European Patent Application No. 20190445.5.

* cited by examiner

FIG.2

SIGN MODEL STORAGE UNIT 200

| PHYSICAL CONDITION ABNORMALITY NAME (201) | SIGN MODEL PARAMETER (202) |
|---|---|
| *** | *** |
| *** | *** |
| ⋮ | ⋮ |

FIG.3

VITAL SIGN STORAGE UNIT 300

| USER ID (301) | TIME(START AND END) (302) | DATA LENGTH(RECORDING TIME AND SAMPLING CYCLE) (303) | DETECTED PHYSICAL CONDITION ABNORMALITY (304) | VITAL SIGN (305) |
|---|---|---|---|---|
| u001 | 2019/05/05 11:20:22, 2019/05/05 11:45:22 | 25 MINUTES, INTERVAL OF ONE SECONDS | LOW AROUSAL | *** |
| ⋮ | ⋮ | ⋮ | ⋮ | ⋮ |

FIG.5

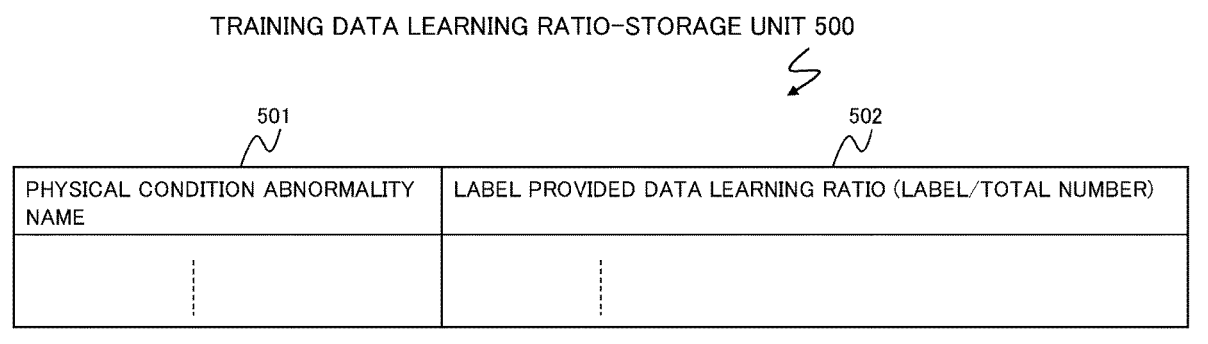

TRAINING DATA LEARNING RATIO-STORAGE UNIT 500

| PHYSICAL CONDITION ABNORMALITY NAME (501) | LABEL PROVIDED DATA LEARNING RATIO (LABEL/TOTAL NUMBER) (502) |
|---|---|
| ⋮ | ⋮ |

STATE EXTRAPOLATION DEVICE, STATE EXTRAPOLATION PROGRAM, AND STATE EXTRAPOLATION METHOD

TECHNICAL FIELD

The present invention relates to a technique of a state extrapolation device, a state extrapolation program, and a state extrapolation method. This application claims the priority based on the Japanese Patent Application No. 2019-154470 filed on Aug. 27, 2019. The entire contents of which are incorporated herein by reference for all purpose.

BACKGROUND ART

As a background art, JP 2018-127112 A (hereinafter, referred to as PTL 1) is known. PTL 1 describes that "[Problem] To provide an arousal level extrapolation device capable of extrapolating an arousal level of a driver of a vehicle that has an automatic drive mode and a manual drive mode with high accuracy. [Solution] A vehicle can be switched between an automatic drive mode and a manual drive mode, and includes: a vehicle behavior detection unit that detects drive information of the vehicle; a first arousal level recognition unit that recognizes a first arousal level of a driver from the detected drive information; a vital sign detection unit that detects one or more vital signs of the driver; a second arousal level recognition unit that recognizes a second arousal level of the driver from the one or more detected vital signs of the driver; and an arousal level extrapolation unit that extrapolates a third arousal level of the driver from at least one of the recognized first arousal level and second arousal level. The arousal level extrapolation unit extrapolates the third arousal level from the first arousal level and the second arousal level in the manual drive mode, and extrapolates the third arousal level from the second arousal level in the automatic drive mode".

PTL 1: JP 2018-127112A

SUMMARY

In PTL 1, for example, an arousal level can be extrapolated only after a user already feels sleepiness and an abnormality occurs in behavior of a vehicle and a drive operation. Thus, an object of the present invention is to provide a technique for more appropriately extrapolating a sign of a state that may affect a user operation.

The present invention includes a plurality of solutions to at least a part of the above-mentioned problem. One example of the solutions is as follows. In order to solve the problem described above, a state extrapolation device according to the present invention includes a vital sign acquisition unit that acquires a vital sign of a user, and a sign detection unit that uses a learned model that has learned, as training data, sign data about the vital sign related to a predetermined physical condition abnormality, and detects a sign by determining whether or not the vital sign of the user corresponds to a sign of the predetermined physical condition abnormality.

The invention of the present application can more appropriately extrapolate a sign of a state that may affect a movement of a user. A problem, configuration, and effect other than those described in the above will be apparent from the description of embodiments given below.

BRIEF DESCRIPTION OF DRAWINGS

FIG. 2 is a diagram illustrating an example of a data structure of a sign model storage unit.

FIG. 3 is a diagram illustrating an example of a data structure of a vital sign storage unit.

FIG. 5 is a diagram illustrating an example of a data structure of a training data learning ratio-storage unit.

DESCRIPTION OF EMBODIMENTS

Figure 1:
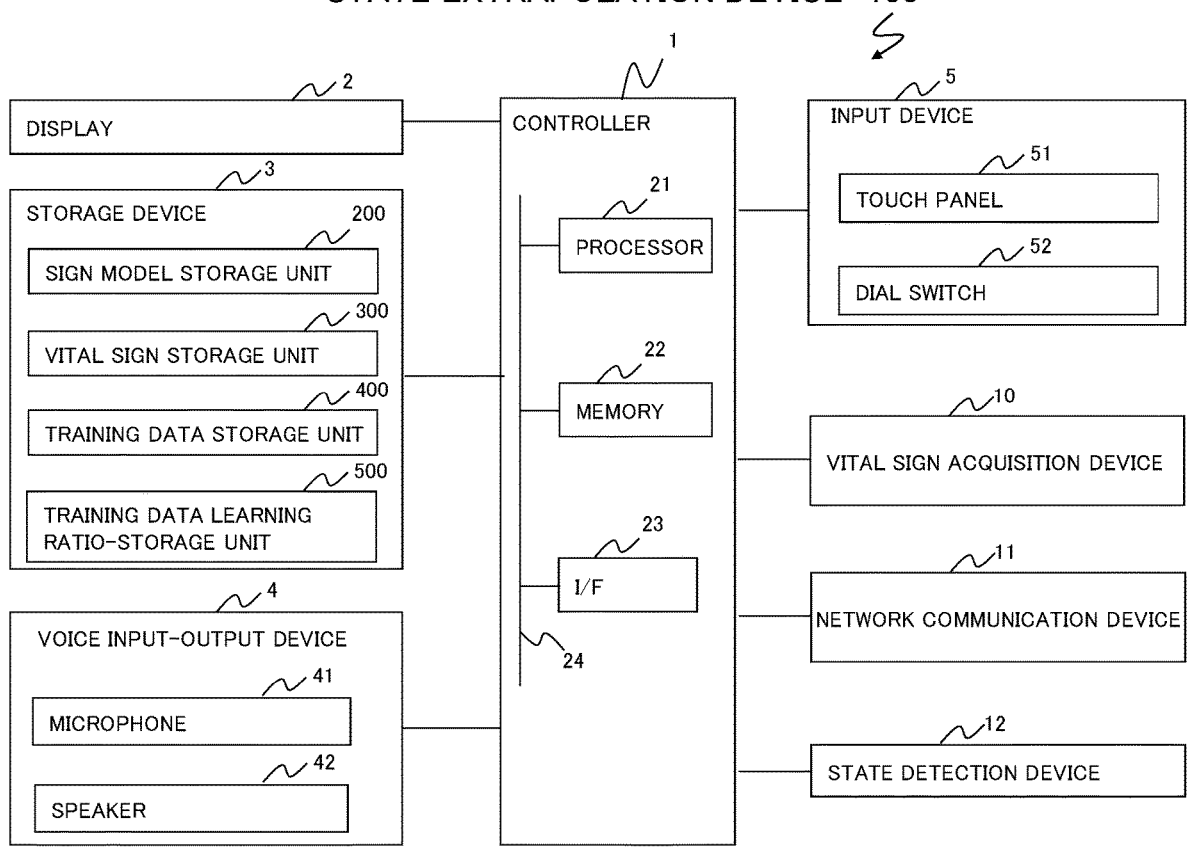
FIG. 1 is a diagram illustrating an example of a structure of a state extrapolation device to which an embodiment according to the present invention is applied.

Hereinafter, an example in which a state extrapolation device 100 according to the present invention is applied to a vehicle-mounted device will be described with reference to drawings. However, the present invention is not limited to the vehicle-mounted device, and can also be applied to a device used during an operation of an object that requires caution in operating. Examples of such a device include, for example, a device used for driving, operating, and riding on a movable body such as an aircraft, a train, and a ship, or a heavy machine such as a power shovel, a crane, and an excavator.

Note that FIGS. 1 to 14 do not illustrate the whole configuration of the state extrapolation device 100, and illustrate the configuration while appropriately omitting a part of the configuration for facilitating understanding. Note that, in all drawings for describing embodiments, the same member is provided with the same reference sign in principle, and repetitive description thereof may be omitted. In the following embodiments, it is needless to say that some components of the embodiments (also including an element step and the like) is not necessarily essential except when specified otherwise, a component is conceivably essential theoretically and clearly, and the like.

When "formed from A", "formed of A", "having A", and "including A" are referred, it is needless to say that an element other than A is not eliminated except when specified otherwise that A is the only element, and the like. Similarly, in the following embodiments, when a shape, a positional relationship, and the like of a component and the like are referred, a shape and the like substantially resembling or similar to the shape and the like are included except when specified otherwise, it is not conceivably true theoretically and clearly, and the like.

As an expression according to the present invention, "state information" basically indicates information acquired by visually observing a human body of a user from the outside, and a "physical condition abnormality" indicates a state deviating from an assumed normal state among states comprehensively determined from states acquired by being visually observed from the outside. For example, "state information" includes information in general that can be quantified by objectively observing a living body, such as a "frequency of blinks", "yawning", a "movement amount of a viewpoint", "swaying and tilting of a body", "snoring", "stiffening (no posture change)", and "convulsions".

Then, a "physical condition abnormality" includes a comprehensive abnormality in general in terms of a physical condition that may adversely affect an operation or an exercise movement, such as "low arousal (including sleepiness)", "high arousal (including abnormal uplift and the like)", "syncope (including an involuntary motion such as epilepsy and a faint)", a "heart attack", and "autonomic imbalance (including a metabolic disorder and the like)". Note that it is needless to say that, except when specified otherwise that various types of such states of a living body and information about the states are the only element, and the like, the other elements are not eliminated.

Furthermore, a "vital sign" indicates information acquired by measuring a human body of a user from the outside. For example, the "vital sign" includes a brain wave, a pulse wave, blood pressure, body temperature, and the like. Note that it is needless to say that, except when specified otherwise that various types of such vital signs are the only element, and the like, the other elements are not eliminated.

In general, when a certain physical condition abnormality occurs, it has been clear that a characteristic change appears in a vital sign in advance. For example, for a "low arousal (sleepiness)", it has been clear that an increase in frequency of blinks and an increase in yawning correspond to symptoms that can be visually observed, and a heart rate decreases as a sign in advance (probably, before about several tens of minutes).

It has been clear that an occurrence of "epilepsy" corresponds to a physical condition abnormality that is less likely to be visually observed such that a disturbance in brain wave increases, and a heart rate is disturbed (HRV: heart rate variability (fluctuation in heart rate, fluctuation in milliseconds units at RR intervals)) as a sign in advance (probably, before about eight minutes).

In other words, when a sign before an occurrence of such a physical condition abnormality can be extrapolated from a vital sign, various types of measures such as warning may be taken before the occurrence.

FIG. 1 is a diagram illustrating an example of a structure of a state extrapolation device to which an embodiment according to the present invention is applied. The state extrapolation device 100 removably installed on a movable body is an information processing device capable of acquiring a vital sign and state information. However, the state extrapolation device 100 being a target of the invention of the present application is not limited to the state extrapolation device 100 illustrated in FIG. 1. For example, the state extrapolation device 100 may be various types of control apparatuses incorporated in a movable body and a heavy machine.

The state extrapolation device 100 includes a controller 1, a display 2, a storage device 3, a voice input-output device 4 (including a microphone 41 as a voice input device and a speaker 42 as a voice output device), an input device 5, a vital sign acquisition device 10, a network communication device 11, and a state detection device 12.

The controller 1 is a central unit that performs various processing. For example, the controller 1 calculates a current location, based on information output from a vehicle speed sensor, an acceleration sensor, and a global positioning system (GPS) reception device that are not illustrated. The controller 1 reads map data and the like needed for display from the storage device 3, based on the acquired information about the current location.

The controller 1 deploys graphics of the read map data, superimposes a mark indicating the current location on the map data, and causes the display 2 to display the map data. The controller 1 uses the map data and the like stored in the storage device 3, and searches for a recommended route being an optimum route that connects the current location or a departure location designated by a user and a destination (or a transit location and a stopping place). The controller 1 guides the user by using the speaker 42 and the display 2.

The controller 1 of the state extrapolation device 100 is configured to be connected to each of the devices with a bus 24. The controller 1 includes a processor 21 that performs various processing such as a numerical operation and controlling of each of the devices, a memory 22 that stores map data read from the storage device 3, arithmetic data, and the like, and an interface (I/F) 23 for connecting various types of hardware to the controller 1.

The display 2 is a unit that displays graphics information generated by the controller 1 and the like. The display 2 is formed of a liquid crystal display, an organic electro luminescence (EL) display, or the like. A head-up display, a meter panel, a center console, and the like are included in the display 2. The display 2 may display information on a communication terminal such as a smartphone via communication.

The storage device 3 is formed of a storage medium that enables at least reading and writing, such as a hard disk drive (HDD), a solid state drive (SSD), a non-volatile memory card.

The storage medium stores map data (including link data about a link constituting a road on a map and a link cost as a reference) as a reference needed for a normal route search device, a sign model storage unit 200, a vital sign storage unit 300, a training data storage unit 400, and a training data learning ratio-storage unit 500.

FIG. 2 is a diagram illustrating an example of a data structure of the sign model storage unit 200. The sign model storage unit 200 stores a physical condition abnormality name 201 and a sign model parameter 202 in association with each other. The physical condition abnormality name 201 is information that specifies a physical condition abnormality as a detection target of a user, and includes a comprehensive "physical condition abnormality" in general that may adversely affect an operation or driving, such as "low arousal (including sleepiness)", "high arousal (including abnormal uplift and the like)", "syncope (including an involuntary motion such as epilepsy and a faint)", a "heart attack", and "autonomic imbalance (including a metabolic disorder and the like)", for example.

The sign model parameter 202 is a parameter acquired by modeling a characteristic of a change in vital sign of types acquired in the vital sign acquisition device 10, which is a sign portion for each physical condition abnormality. Herein, a sign model is a learned model called a neural network constituted by using a technique of machine learning called deep learning, which is not limited thereto. For example, a sign may be detected by using various types of artificial intelligence (AI) such as a Bayes classifier and a support vector machine.

FIG. 3 is a diagram illustrating an example of a data structure of the vital sign storage unit 300. The vital sign storage unit 300 stores a user ID 301, a time (start and end) 302, a data length (recording time and sampling cycle) 303, a detected physical condition abnormality 304, and a vital sign 305 in association with one another.

The user ID 301 is information that specifies a user. The time (start and end) 302 is information that specifies a recording start time and a recording end time of a vital sign. The data length (recording time and sampling cycle) 303 is information that specifies time from a recording start until a recording end of a vital sign, and a sampling cycle. The detected physical condition abnormality 304 is information that specifies a physical condition abnormality associated with a vital sign. The vital sign 305 is information in which recording of a predetermined vital sign and a vital sign ID that specifies the predetermined vital sign are associated with each other.

Figure 4:
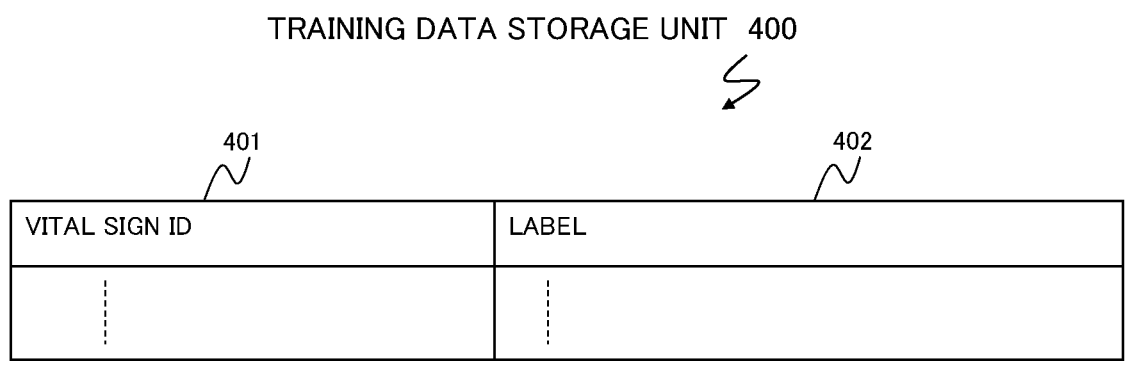
FIG. 4 is a diagram illustrating an example of a data structure of a training data storage unit.

FIG. 4 is a diagram illustrating an example of a data structure of the training data storage unit 400. The training data storage unit 400 stores a vital sign ID 401 and a label 402 in association with each other. The vital sign ID 401 is information that specifies a vital sign. The label 402 is information that specifies, when a vital sign specified by the vital sign ID 401 indicates a sign of a predetermined physical condition abnormality, the physical condition abnormality. When a vital sign does not indicate a sign of a predetermined physical condition abnormality, in other words, when a vital sign is a normal vital sign without a physical condition abnormality, the label 402 is blank (null).

FIG. 5 is a diagram illustrating an example of a data structure of the training data learning ratio-storage unit 500. The training data learning ratio-storage unit 500 stores a physical condition abnormality name 501 and a label provided data learning ratio (label/total number) 502 in association with each other. The physical condition abnormality name 501 is information that specifies a physical condition abnormality. The label provided data learning ratio (label/total number) 502 is information indicating a ratio of a breakdown of training data used in machine learning of a sign model for each physical condition abnormality specified by the physical condition abnormality name 501.

Data provided with a label are namely vital sign data in a predetermined period immediately before occurrence of a physical condition abnormality, and are data associated with the physical condition abnormality that occurs. Data without a label are vital sign data in a predetermined period when a physical condition abnormality does not occur subsequently. For example, when the label provided data learning ratio (label/total number) 502 of training data used for constructing a sign model of a physical condition abnormality of "low arousal" is "1:2", it indicates that label provided data of "low arousal" accounts for substantially half of a total number of pieces of the training data used for learning.

Referring back to FIG. 1, and description will be given. The voice input-output device 4 includes the microphone 41 as the voice input device, and the speaker 42 as the voice output device. The microphone 41 acquires voice outside the state extrapolation device 100, such as voice from a user or another passenger.

The speaker 42 outputs a message to a user, which is generated in the controller 1, as voice. The microphone 41 and the speaker 42 are separately disposed on predetermined areas of a movable body. However, the microphone 41 and the speaker 42 may be housed in one housing. The state extrapolation device 100 can include a plurality of the microphones 41 and the speakers 42.

The state extrapolation device 100 may output voice from a microphone and a speaker of another device (for example, a smartphone and the like in wired connection with a universal serial bus (USB) cable and the like, and a smartphone and the like in wireless connection with Wifi, Bluetooth (registered trademark), and the like) to be connected without including the microphone 41 and the speaker 42.

The input device 5 is a device that receives an instruction from a user via an operation by the user. The input device 5 is formed of a touch panel 51, a dial switch 52, a scroll key and a scale change key being other hard switches (not illustrated), and a gesture sensor that detects a gesture of a user, and the like. The input device 5 includes a remote controller that can remotely perform an operation instruction on the state extrapolation device 100. The remote controller includes the dial switch, the scroll key, the scale change key, and the like, and can transmit information acquired by operating each of the keys and the switch to the state extrapolation device 100.

The touch panel 51 is installed on a display surface side of the display 2, and allows a display screen to be seen therethrough. The touch panel 51 specifies a touch position corresponding to XY coordinates on an image displayed on the display 2, converts the touch position into coordinates, and outputs the coordinates. The touch panel 51 is formed of a pressure sensitive input detection element, an electrostatic input detection element, or the like. Note that the touch panel 51 may be able to achieve a multi-touch that can simultaneously detect a plurality of touch positions.

The dial switch 52 is configured to be rotatable clockwise and counterclockwise, emits a pulse signal by every predetermined angle of rotation, and outputs the pulse signal to the controller 1. The controller 1 obtains a rotation angle from the number of pulse signals.

The vital sign acquisition device 10 is a device that acquires a vital sign such as a pulse wave of a user. With regard to the acquisition of information about a pulse wave, a photoelectric pulse wave method such as a reflection pulse wave measurement, for example, can be adopted, which is not limited thereto. Various types of measurement methods such as a transmission pulse wave measurement, phonocardiography, and electrocardiography may be adopted.

An appropriate sensor according to a use environment, such as a Doppler sensor and a mat (piezoelectric) sensor, for example, is used for the vital sign acquisition device 10. Hardware of the vital sign acquisition device 10 may include a sensor attached to a smart watch, a sheet, a handle, a pillar, and the like, and is configured to perform transmission to the state extrapolation device 100 via a wireless or wired communication path such as Bluetooth and a USB cable.

The network communication device 11 is a device that connects the state extrapolation device 100 to a network corresponding to a controller area network (CAN) being a control network standard in a movable body (not illustrated), and the like, and performs communication by exchanging a CAN message and the like with an electronic control unit (ECU) being another control device in the movable body connected to the network. The network communication device 11 can connect the state extrapolation device 100 to a cell phone network (not illustrated), and perform communication with another device connected to the cell phone network.

The state detection device 12 is a device that acquires information about an occurrence state of a predetermined physical condition abnormality from a face image and the like of a user. With regard to the acquisition of information about an occurrence state of a predetermined physical condition abnormality, the state detection device 12 acquires image information about an area that can be visually observed from the outside, such as a face, for example, by photographing and the like, analyzes the image to acquire the information about the occurrence state. For example, the state detection device 12 detects a frequency of blinks, yawning, PERCLOS (percent of the time eyelids are closed), microsaccade (eye involuntary movement), head sway, and the like, determines whether or not the detected information corresponds to a symptom of "low arousal", and detects a state of the "low arousal". Note that an existing technique is adopted for specific mechanism and algorithm that acquire information about an occurrence state by the state detection device 12.

Figure 6:
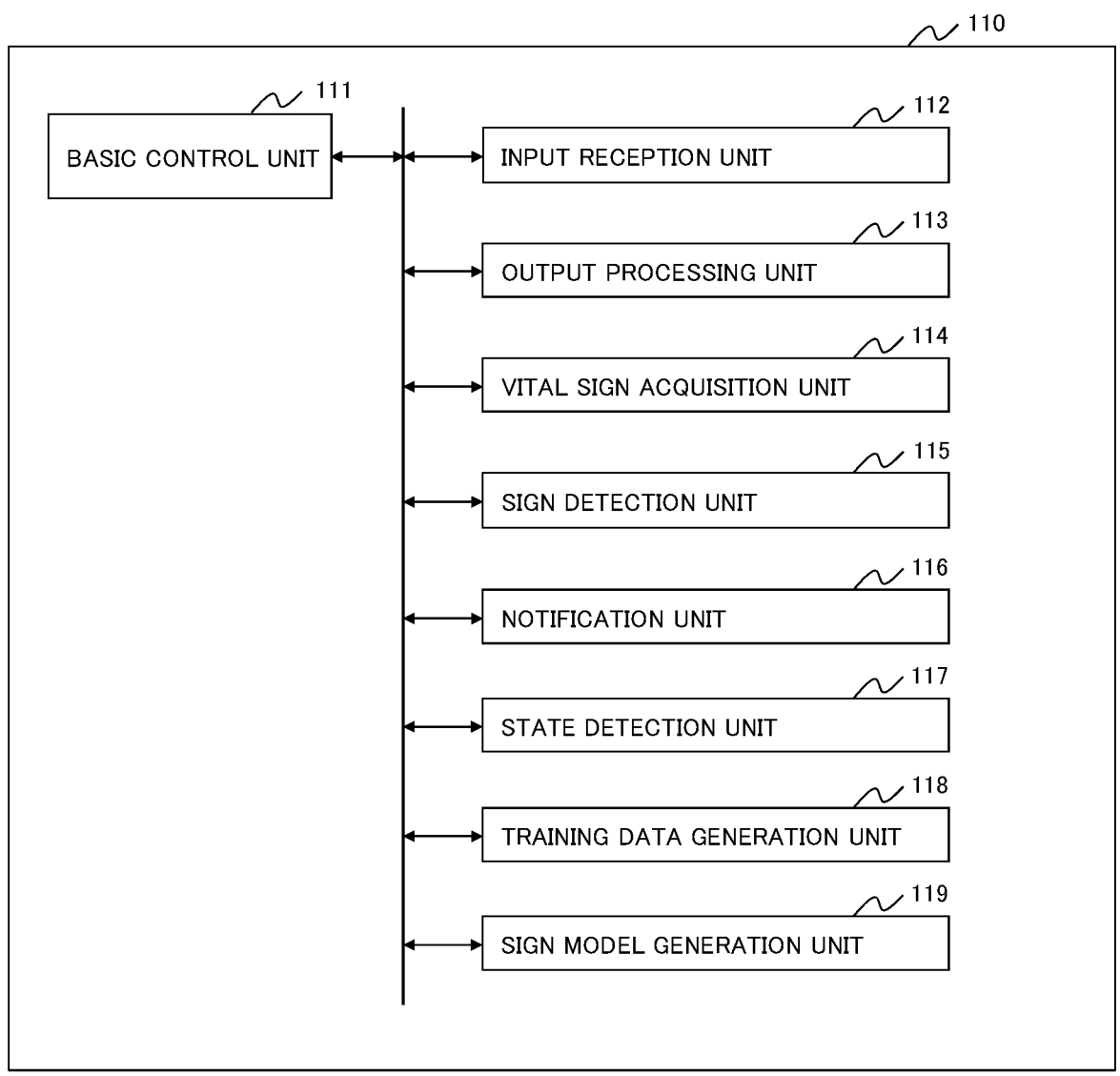
FIG. 6 is a diagram illustrating an example of a functional configuration of a controller.

FIG. 6 is a diagram illustrating a functional configuration of the controller 1. The controller 1 includes a basic control unit 111, an input reception unit 112, an output processing unit 113, a vital sign acquisition unit 114, a sign detection unit 115, a notification unit 116, a state detection unit 117, a training data generation unit 118, and a sign model generation unit 119.

The basic control unit 111 is a central functional unit that performs various processing, and controls an operation of the other functional units (the input reception unit 112, the output processing unit 113, the vital sign acquisition unit 114, the sign detection unit 115, the notification unit 116, the state detection unit 117, the training data generation unit 118, and the sign model generation unit 119) according to a processing content. The basic control unit 111 also takes on processing of acquiring information of various types of sensors, a GPS reception device, and the like, and specifying a current location by performing map matching processing and the like.

The input reception unit 112 receives an input instruction from a user being input via the input device 5 or the microphone 41, and transmits, to the basic control unit 111, a request for execution processing corresponding to a request content together with a coordinate position of a touch and voice information that are information related to the input instruction. For example, when a user requests execution of certain processing, the input reception unit 112 requests the requested instruction to the basic control unit 111. In other words, it can be said that the input reception unit 112 is an instruction reception unit that receives an instruction by an operation of a user.

The output processing unit 113 receives information constituting a screen to be displayed, such as polygon information, for example, converts the information into a signal for drawing on the display 2, and performs an instruction of drawing on the display 2.

The vital sign acquisition unit 114 establishes communication with the vital sign acquisition device 10, acquires information about a pulse wave and the like being a vital sign acquired by the vital sign acquisition device 10 by always performing communication or intermittently performing communication, and holds the information together with history information in a certain period on the RAM 22 or the storage device 3.

Note that, when an acquired vital sign deviates from a predetermined range, the vital sign acquisition unit 114 causes the notification unit 116 to make a notification, and deletes the vital sign. In this way, a critical condition of a user due to an abnormality can be found at an early stage, and a decrease in accuracy of detecting a sign due to abnormality data mixed in training data can also be avoided.

The sign detection unit 115 uses a learned model (sign model) that has learned, as training data, sign data about a vital sign related to a predetermined physical condition abnormality, and detects a sign by determining whether or not the vital sign acquired by the vital sign acquisition unit 114 corresponds to a sign of the predetermined physical condition abnormality.

More specifically, when the sign detection unit 115 acquires a vital sign, the sign detection unit 115 performs formatting of data by performing deletion of an outlier, complementing of data, and the like on the vital sign, and calculates a predetermined index value (such as interval frequency resolution and HRV, for example). Then, the sign detection unit 115 causes the sign model being the learned model to detect a sign of a physical condition abnormality, and causes the notification unit 116 to make a notification about detection of the sign when the sign is detected.

The notification unit 116 receives an instruction from a functional unit such as the sign detection unit 115, and notifies a predetermined target by a set predetermined method by outputting a predetermined message and the like by voice or displaying the predetermined message and the like, outputting an alarm sound, sending an e-mail, and using various types of messaging including a social networking service (SNS) and the like. Still alternatively, the notification unit 116 may make a notification by slightly vibrating a seating surface and a back of a seat, an arm rest, a steering wheel, and the like that are used by a user.

The state detection unit 117 detects an occurrence state of the above-described predetermined physical condition abnormality of the user. The state detection unit 117 acquires information about the occurrence state of the predetermined physical condition abnormality acquired from a face image and the like of the user by the state detection device 12. For example, the state detection unit 117 detects a comprehensive physical condition abnormality that may adversely affect an operation or driving, such as "low arousal (including sleepiness)", "high arousal (including abnormal uplift and the like)", "syncope (including an involuntary motion such as epilepsy and a faint)", a "heart attack", and "autonomic imbalance (including a metabolic disorder and the like)".

The training data generation unit 118 generates, when the state detection unit 117 detects the occurrence state, training data by using first information being a vital sign of the user provided with a label in a predetermined period immediately before the occurrence state, and second information being a vital sign of the user in the predetermined period when the occurrence state is not detected. Note that the training data generation unit 118 generates training data so as to set the first information and the second information at a predetermined ratio (desirably, 1:1).

The training data generation unit 118 specifies a data length (recording period and sampling cycle) of each of the first information and the second information according to a physical condition abnormality.

When the training data generation unit 118 receives an input indicating a disagreement with a sign detected by the sign detection unit 115, for example, an input from the user that "not sleepy" after a sign of "low arousal" is notified, in a case where the state detection unit 117 does not subsequently detect an occurrence state within a predetermined period, the training data generation unit 118 generates training data in which a vital sign when the sign is detected is set to the second information, in other words, a vital sign when a state is not abnormal in order to improve accuracy of detecting a sign.

The sign model generation unit 119 generates a learned model as a sign model by using the training data generated by the training data generation unit 118 for machine learning. Processing of generating the sign model itself is processing basically similar to existing machine learning.

Each of the functional units of the controller 1 described above, specifically, the basic control unit 111, the input reception unit 112, the output processing unit 113, the vital sign acquisition unit 114, the sign detection unit 115, the notification unit 116, the state detection unit 117, the training data generation unit 118, and the sign model generation unit 119 is constructed by the processor 21 reading and executing a predetermined program. Thus, the memory 22 stores the program for implementing processing of each of the functional units.

Note that each of the components described above is acquired by classifying the configuration of the state extrapolation device 100 according to a main processing content for facilitating understanding. Thus, how the components are classified and referred to do not limit the invention of the present application. The configurations of the state extrapolation device 100 can also be further classified into more components according to a processing content. The components can be classified so that one component performs more processing.

Each of the functional units may be constructed by hardware (a programmable logic device (PLD) such as an ASIC, a graphics processing unit (GPU), and a field-programmable gate array (FPGA)). Processing of each of the functional units may be performed by one piece of hardware, or may be performed by a plurality of pieces of hardware. The processing of each of the functional units may be transferred to an external cloud server and the like via the network communication device 11, or data in the storage device 3 may be stored in the external cloud server and the like via the network communication device 11.

Figure 7:
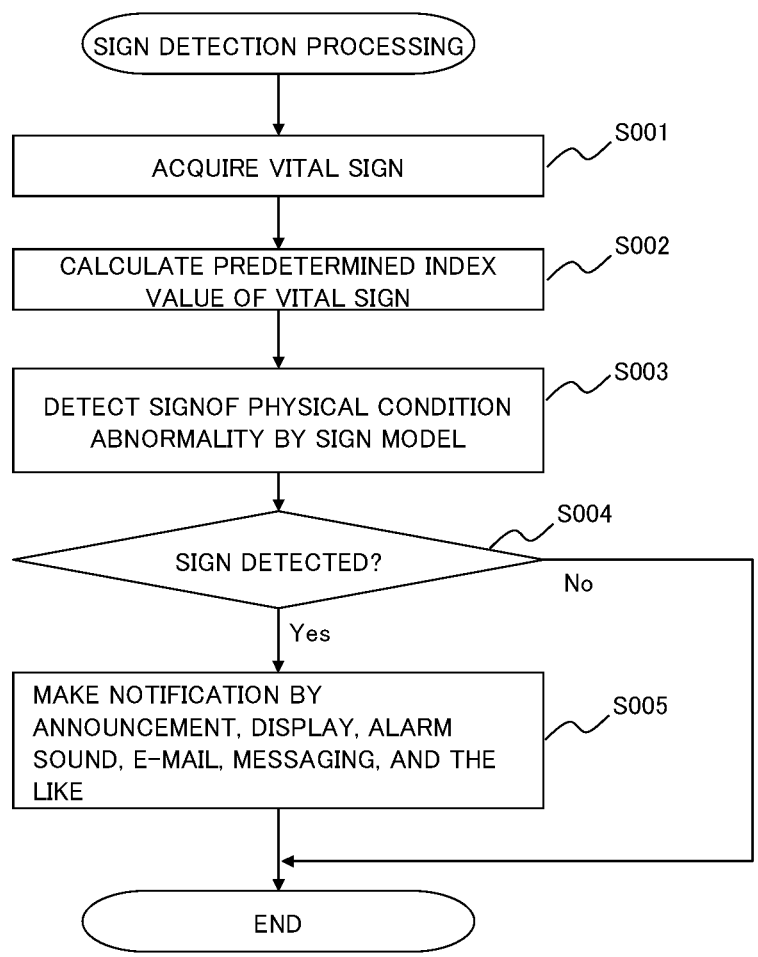
FIG. 7 is a diagram illustrating an example of a flow of sign detection processing.

[Description of Operation] Next, an operation related to sign detection processing will be described. FIG. 7 is a diagram illustrating an example of a flow of the sign detection processing. The sign detection processing starts at a predetermined interval (for example, at a predetermined interval such as once in one second, once in five seconds, or once in one minute) when the state extrapolation device 100 is activated.

First, the vital sign acquisition unit 114 acquires a vital sign (step S001). Specifically, the vital sign acquisition unit 114 establishes communication with the vital sign acquisition device 10, acquires information about a pulse wave being a vital sign acquired by the vital sign acquisition device 10 by always performing communication or intermittently performing communication, and holds the information together with history information in a certain period on the RAM 22 or the storage device 3.

Then, the sign detection unit 115 calculates a predetermined index value of the vital sign (step S002). Specifically, the sign detection unit 115 acquires the vital sign from the vital sign acquisition unit 114, performs formatting of data by performing deletion of an outlier, complementing of data, and the like on the vital sign, and calculates a predetermined index value (such as interval frequency resolution and HRV, for example).

Then, the sign detection unit 115 detects a sign of a physical condition abnormality by a sign model (step S003). Specifically, the sign detection unit 115 uses a learned model (sign model) that has learned, as training data, sign data about a vital sign corresponding to each physical condition abnormality name 201 in the sign model storage unit 200, and detects a sign by determining whether or not the vital sign acquired by the vital sign acquisition unit 114 corresponds to a sign of a predetermined physical condition abnormality.

Then, the sign detection unit 115 determines whether or not the sign is detected (step S004). Specifically, the sign detection unit 115 determines that the sign is detected when the sign of each physical condition abnormality is detected from the sign model for each physical condition abnormality. However, this is not restrictive, and it may be determined that the sign is detected by whether or not a combination of detection of several physical condition abnormalities satisfies a predetermined condition. When the sign is not detected (in a case of "No" in step S004), the sign detection unit 115 terminates the sign detection processing.

When the sign is detected (in a case of "Yes" in step S004), the sign detection unit 115 makes a notification by an announcement, a display, an alarm sound, an e-mail, messaging, and the like (step S005). Specifically, the sign detection unit 115 causes the notification unit 116 to notify detection of the sign.

The example of the flow of the sign detection processing is described above. The sign detection processing can more appropriately extrapolate a state that may affect a user operation, in other words, a sign of a physical condition abnormality.

Note that the above-described sign detection processing determines a binary of whether or not detection of a sign is performed, which is not limited thereto. The sign detection processing can also achieve a determination in many stages by using a likelihood of a sign model. For example, an arousal level can also be determined in a plurality of stages.

Figure 8:
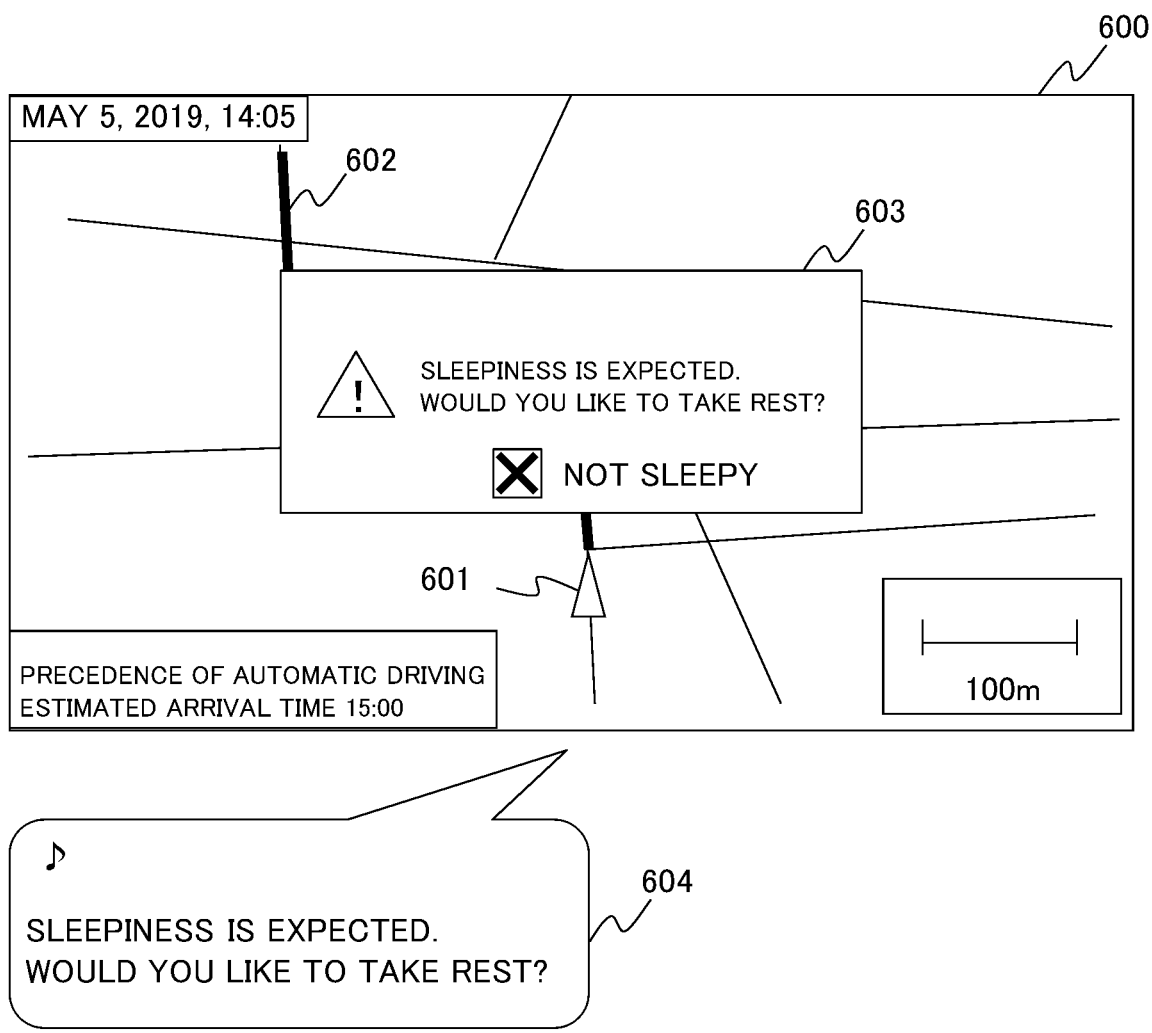
FIG. 8 is a diagram illustrating an example of an arousal abnormality notification screen.

FIG. 8 is a diagram illustrating an example of an arousal abnormality notification screen. An arousal abnormality notification screen 600 is an example of a screen output in step S005 in the sign detection processing.

The arousal abnormality notification screen 600 includes a so-called navigation screen including a peripheral map mainly including a marker 601 indicating an own car position and a recommended route display 602 indicating a road to be traveled.

The navigation screen is a screen of application software activated when the state extrapolation device 100 is activated. Thus, the navigation screen is not restrictive, and may be a screen of other application software. For example, a moving image display screen may be used, and an operation screen for musical reproduction, or a menu screen, a setting screen, and the like of the state extrapolation device 100 indicated by the basic control unit 111 may be used.

Then, the arousal abnormality notification screen 600 displays a message box 603 that displays a message. Furthermore, a voice 604 of a message having a similar content is output. It is desirable that the message, such as "Sleepiness is expected. Take a break?", includes a point that a sign of a physical condition abnormality is detected, the physical condition abnormality having the sign detected, and an action for handling an occurrence of the physical condition abnormality.

The message box 603 includes a button that receives an input of a disagreement with a notified content. For example, the arousal abnormality notification screen 600 in which a sign of sleepiness is detected includes a region in which an input of a disagreement, such as "Not sleepy", is received.

When a touch input is performed on the region in which an input of a disagreement is received, in a case where a physical condition abnormality related to the sign does not subsequently occur in a predetermined period, the sign is regarded as false detection, and calibration processing described below of changing training data can be performed.

Figure 9:
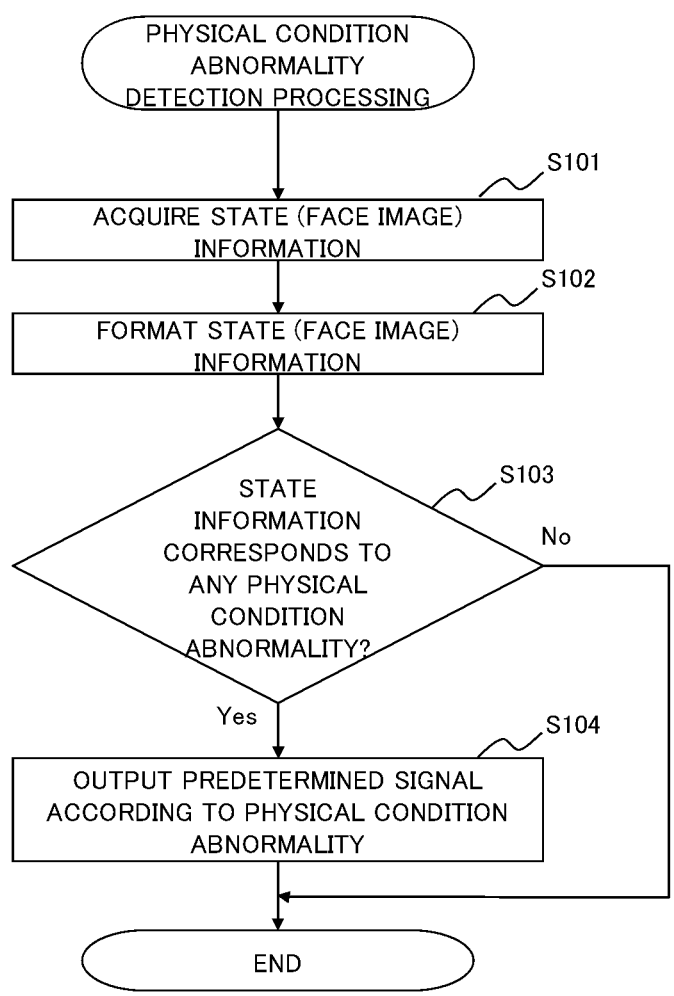
FIG. 9 is a diagram illustrating an example of a flow of physical condition abnormality detection processing.

FIG. 9 is a diagram illustrating an example of a flow of physical condition abnormality detection processing. The physical condition abnormality detection processing starts at a predetermined interval (for example, at a predetermined interval such as once in one second, once in five seconds, or once in one minute) when the state extrapolation device 100 is activated.

First, the state detection unit 117 acquires state (face image) information (step S101). Specifically, the state detection unit 117 establishes communication with the state detection device 12, acquires information about a face image being state information acquired by the state detection device 12 by always performing communication or intermittently performing communication, and holds the information together with history information in a certain period on the RAM 22 or the storage device 3.

Then, the state detection unit 117 formats the state (face image) information (step S102). Specifically, the state detection unit 117 formats an image by performing deletion of noise, complementing of data, and the like on the state information.

Then, the state detection unit 117 determines whether or not the state information corresponds to any physical condition abnormality (step S103). Specifically, the state detection unit 117 acquires, from the state detection device 12, a frequency of blinks, yawning, PERCLOS (percent of the time eyelids are closed), microsaccade (eye involuntary movement), head sway, and the like, and a determination result of whether or not the state information corresponds to a symptom of a physical condition abnormality, and determines whether or not the state information corresponds to any physical condition abnormality. When the state information does not correspond to a physical condition abnormality (in a case of "No" in step S103), the state detection unit 117 terminates the physical condition abnormality detection processing.

When the state information corresponds to a physical condition abnormality (in a case of "Yes" in step S103), the state detection unit 117 outputs a predetermined signal according to the physical condition abnormality (step S104). Specifically, the state detection unit 117 outputs a signal according to a content of the physical condition abnormality, namely, the physical condition abnormality that occurs as a detection signal of the physical condition abnormality to the training data generation unit 118 and the like.

The flow of the physical condition abnormality detection processing is described above. According to the physical condition abnormality detection processing, a physical condition abnormality can be notified to the training data generation unit 118 by using state information acquired from the state detection device 12.

Figure 10:
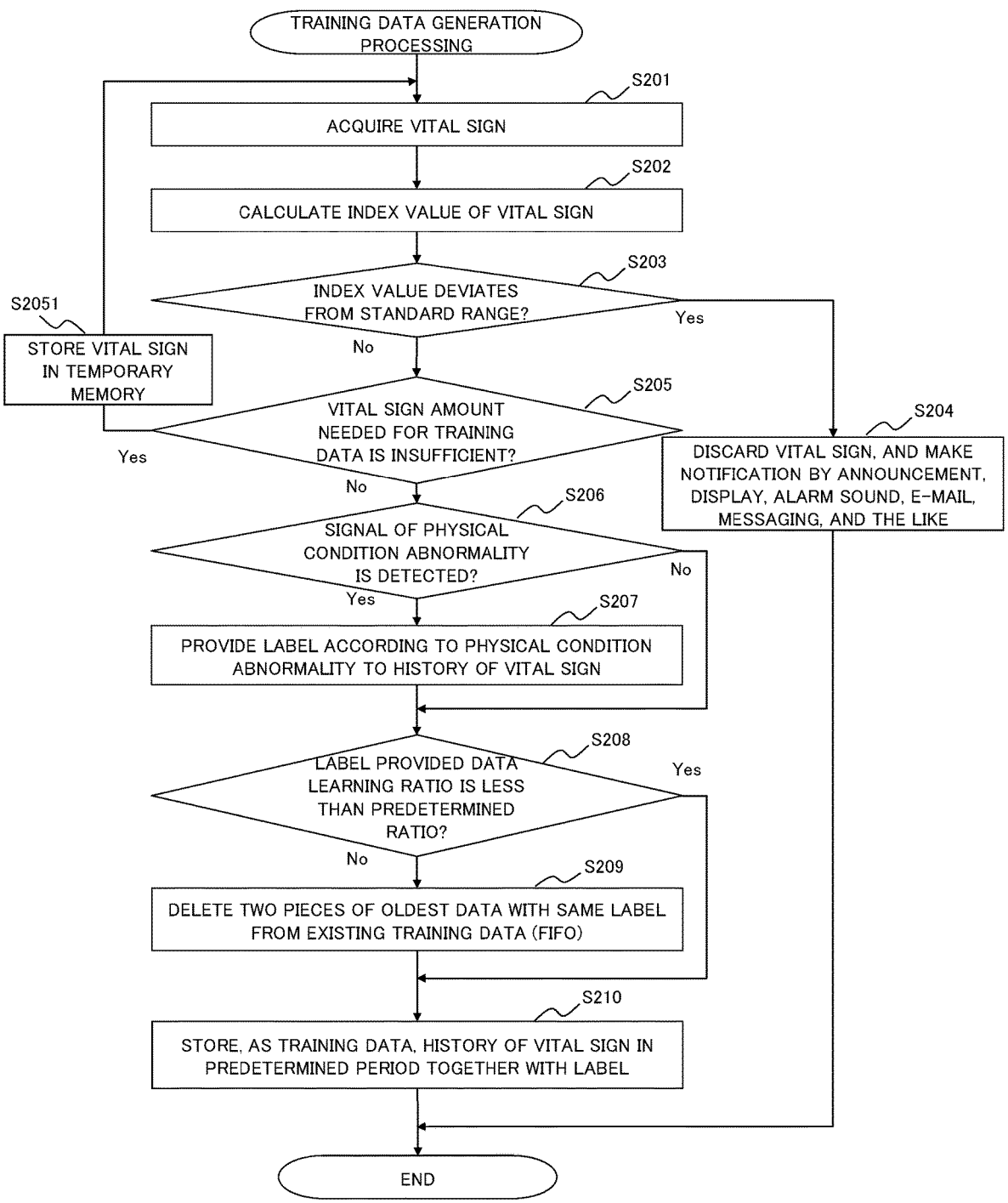
FIG. 10 is a diagram illustrating an example of a flow of training data generation processing.

FIG. 10 is a diagram illustrating an example of a flow of training data generation processing. The training data generation processing starts at a predetermined interval (for example, at a predetermined interval such as once in one second, once in five seconds, or once in one minute) when the state extrapolation device 100 is activated.

First, the vital sign acquisition unit 114 acquires a vital sign (step S201). Specifically, the vital sign acquisition unit 114 establishes communication with the vital sign acquisition device 10, acquires information about a pulse wave being a vital sign acquired by the vital sign acquisition device 10 by always performing communication or intermittently performing communication, and holds the information together with history information in a predetermined period (for example, a period from 40 minutes before a point of processing until the point of processing) on the RAM 22 or the storage device 3.

Then, the sign detection unit 115 calculates a predetermined index value of the vital sign (step S202). Specifically, the sign detection unit 115 acquires the vital sign from the vital sign acquisition unit 114, performs formatting of data by performing deletion of an outlier, complementing of data, and the like on the vital sign, and calculates a predetermined index value (such as interval frequency resolution, a heart rate, and HRV, for example).

Then, the training data generation unit 118 determines whether or not the calculated index value deviates from a standard range (step S203). For example, the training data generation unit 118 determines whether or not the calculated index value deviates from a normal health state.

When the calculated index value deviates from the standard range (in a case of "Yes" in step S203), the vital sign acquisition unit 114 discards the vital sign, and instructs the notification unit 116 to notify that the index value deviates from the standard range by an announcement, a display, an alarm sound, an e-mail, messaging, and the like (step S204). In this way, shortage of a storage capacity of the storage device 3 can be prevented, and a decrease in accuracy of extrapolating a sign can be prevented.

When the calculated index value does not deviate from the standard range (in a case of "No" in step S203), the training data generation unit 118 determines whether or not a vital sign amount (training data length) needed for constructing training data is insufficient (step S205). Specifically, the training data generation unit 118 determines whether or not the history information about the pulse wave held by the vital sign acquisition unit 114 in step S201 has a data length shorter than the data length (recording time and sampling cycle) 303 of training data according to the physical condition abnormality. When the vital sign amount (training data length) needed for constructing the training data is insufficient (in a case of "Yes" in step S205), the training data generation unit 118 stores the acquired vital sign (step S2051), and returns the control to step S201. A storage destination of the vital sign is, for example, a temporary memory (not illustrated) and the like.

When the vital sign amount (training data length) is sufficient for constructing the training data (in a case of "No" in step S205), the training data generation unit 118 determines whether or not a signal of the physical condition abnormality is detected (step S206). Specifically, the training data generation unit 118 determines whether or not a detection signal of the physical condition abnormality is output from the state detection unit 117. When the signal is not yet detected (in a case of "No" in step S206), the training data generation unit 118 proceeds the control to step S208.

When the signal of the physical condition abnormality is detected (in a case of "Yes" in step S206), the training data generation unit 118 provides a label according to the physical condition abnormality to a history of the vital sign (step S207). Specifically, the training data generation unit 118 reads the vital sign from the temporary memory (not illustrated), and holds a vital sign ID in association with a label. The vital sign ID is, for example, a hash value and the like of the vital sign. The training data generation unit 118 provides a label according to the signal of the physical condition abnormality to the training data in association with the vital sign.

Then, the training data generation unit 118 determines whether or not a label provided data learning ratio is less than a predetermined ratio (step S208). Specifically, the training data generation unit 118 refers to the label provided data learning ratio (label/total number) 502 of the physical condition abnormality according to the state, and determines whether or not the label provided data learning ratio (label/total number) 502 is less than 45% (percent), for example. When the label provided data learning ratio is less than the predetermined ratio (in a case of "Yes" in step S208), the training data generation unit 118 proceeds the control to step S210.

When the label provided data learning ratio is not less than the predetermined ratio (in a case of "No" in step S208), the training data generation unit 118 deletes two pieces of oldest data with the same label from existing training data (FIFO: first-in first-out method) (step S209).

For example, when a total number of pieces of training data is 100, label provided data among the training data is 50 (50%), and a threshold value of the label provided learning ratio is 45%, the training data generation unit 118 deletes two pieces of oldest data from the label provided data, which results in a total number of pieces of the training data being 98, and the label provided data among the training data being 48.

Then, the training data generation unit 118 stores, as the training data, a history of the vital sign in the predetermined period together with the label (step S210). Specifically, the training data generation unit 118 cuts a vital sign having a data length needed for the training data among the vital signs acquired in step S201, obtains a hash value as the vital sign ID, provides label information to the training data when the label information is provided, and stores the resultant as one piece of data in the training data storage unit 400.

Then, the training data generation unit 118 calculates the label provided data learning ratio again. For example, when training data provided with a label are additionally stored as one piece of data, a total number of pieces of the training data is 99, label provided data among the training data is 49, and a label provided data learning ratio is 49/99=approximately 49.4%. The training data generation unit 118 stores the label provided data learning ratio in the training data learning ratio-storage unit 500.

The example of flow of the training data generation processing is described above. According to the training data generation processing, when a new vital sign can be acquired, training data can be generated, the training data including, at a predetermined ratio (substantially 1:1), a vital sign provided with a label, in other words, a vital sign being a sign at occurrence of a physical condition abnormality, and a vital sign when the physical condition abnormality does not occur.

The physical condition abnormality detection processing and the training data generation processing can detect an occurrence by using the state detection device being a sensor different from the vital sign acquisition device, and generate training data acquired by performing labeling on a vital sign, and can detect a sign that is difficult to determine from only a vital sign by using a learned model that has machine-learned the training data.

Note that the training data generation processing may be performed in real time, which is not limited thereto. For example, the training data generation processing may be batch-processed collectively in termination processing of the state extrapolation device 100.

Figure 11:
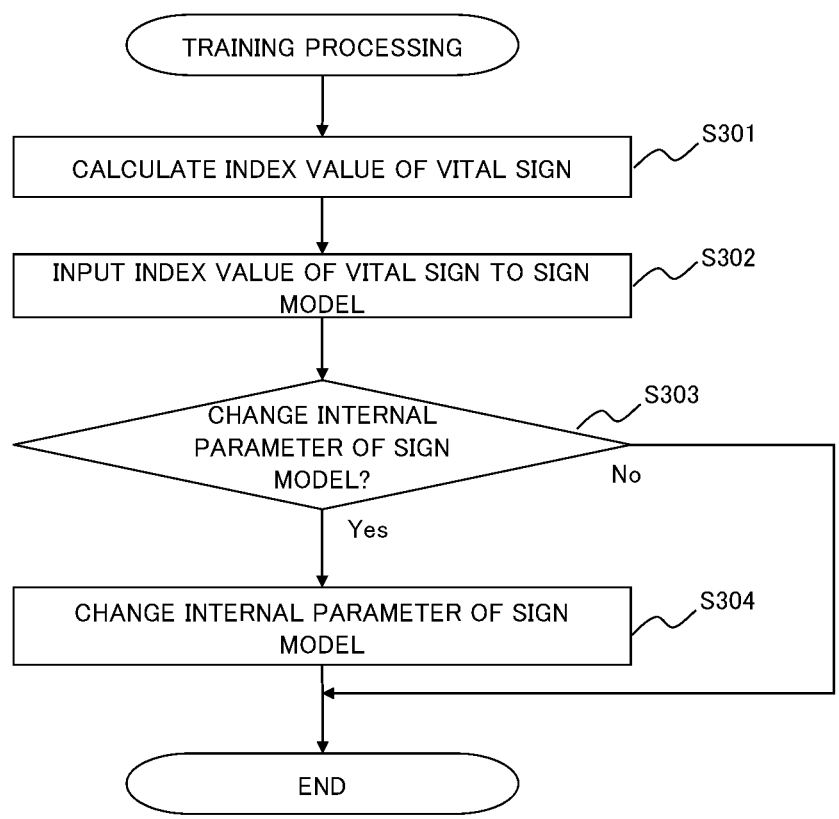
FIG. 11 is a diagram illustrating an example of a flow of training processing.

FIG. 11 is a diagram illustrating an example of a flow of training processing. The training processing starts when the state extrapolation device 100 is activated. Alternatively, the training processing may be performed at irregular intervals such as at timing at which a throughput of the state extrapolation device 100 becomes equal to or less than a predetermined throughput.

First, the sign model generation unit 119 calculates each index value of a vital sign for training data being already generated (step S301). More specifically, the sign model generation unit 119 extracts a vital sign from training data by a predetermined technique, performs formatting of data by performing deletion of an outlier, complementing of data, and the like on the vital sign, and calculates a predetermined index value (such as interval frequency resolution and HRV, for example).

Then, the sign model generation unit 119 performs training of a sign model by the index value of the vital sign. Specifically, the sign model generation unit 119 causes the sign detection unit 115 to extrapolate a solution (for example, a physical condition abnormality with a sign) of the vital sign extracted in step S301 by using an existing sign model as a training target, and acquires the extrapolated solution. For example, the sign model generation unit 119 inputs the index value of the vital sign extracted in step S301 to the sign model (step S302). The input vital sign propagates through internal parameters of the sign model, and the sign model outputs an extrapolation result. For example, when the sign model outputs "0.8" as an extrapolation result, and a label provided to the vital sign of the training data is "1", a difference between the extrapolation result by the sign model and the actual label is "1-0.8", that is, "0.2". When a difference between the extrapolation result by the sign model and the actual label falls below a predetermined value (in a case of "No" in step S303), the sign model generation unit 119 terminates the training processing without changing the internal parameters of the sign model.

When the difference between the extrapolation result by the sign model and the actual label is equal to or more than the predetermined value (in a case of "Yes" in step S303), the sign model generation unit 119 changes the internal parameter(s) of the sign model (step S304). For example, the sign model generation unit 119 can change the internal parameter of the sign model by using back propagation. As necessary, the sign model generation unit 119 can select a vital sign that is a vital sign of the same type as that of a vital sign used for generating the sign model and that is not used for model generation, and input the vital sign to the sign model, and change internal parameters of the sign model, based on a difference between an extrapolation result output from the sign model and an actually provided label. Changing the internal parameters of the sign model by inputting a certain vital sign in such a manner, and then changing the internal parameters of the sign model by inputting a different vital sign that is not the certain vital sign are called a cycle. The number of cycles is appropriately changed by a size of learning data and a configuration of a model.

Figure 12:
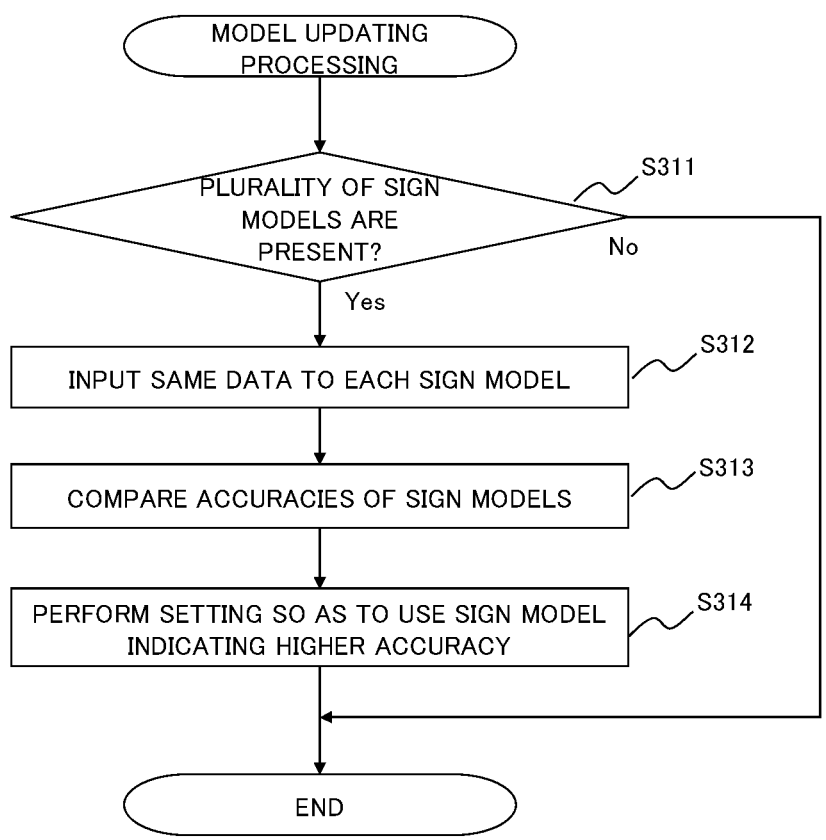
FIG. 12 is a diagram illustrating an example of a flow of model updating processing.

Next, model updating processing will be described. FIG. 12 is a diagram illustrating an example of a flow of the model updating processing. The model updating processing is processing for the purpose of selecting an appropriate model from among a plurality of models generated by performing the training processing for a plurality of times. The model updating processing starts when the state extrapolation device 100 is activated. Alternatively, the model updating processing may start subsequently after the training processing is performed.

First, the sign model generation unit 119 determines whether or not a plurality of models are stored, based on data stored in the sign model storage unit 200 (step S311). When the plurality of sign models are not stored in the sign model storage unit 200 (in a case of "No" in step S311), the sign model generation unit 119 terminates the model updating processing.

When the plurality of sign modes are stored in the sign model storage unit 200 (in a case of "Yes" in step S311), the sign model generation unit 119 inputs an index value based on a vital sign to each of the plurality of sign models (step S312). In the processing, the index value input to each of the sign models is the same data. The vital sign input to the sign model is training data being already stored, and is data that is not used for training of each of the sign models.

Then, the sign model generation unit 119 calculates and compares accuracies of the plurality of sign models to which the same data are input (step S313). For example, there are a method using a percentage of correct answers and a method using a percentage of reproduction as a calculation method used for comparing the accuracies, and any method may be adopted.

Then, the sign model generation unit 119 sets the sign detection unit 115 so as to perform sign detection processing by using the sign model determined to have higher accuracy in step S313 (step S314).

The example of flows of the training processing and the model updating processing are described above. When a new vital sign is acquired, the training processing and the model updating processing can generate a sign model that allows extrapolation of a sign with higher accuracy by using training data including a vital sign provided with a label. Note that the training processing may be performed in real time in addition to the above-described timing, and may be batch-processed collectively in termination processing of the state extrapolation device 100.

Figure 13:
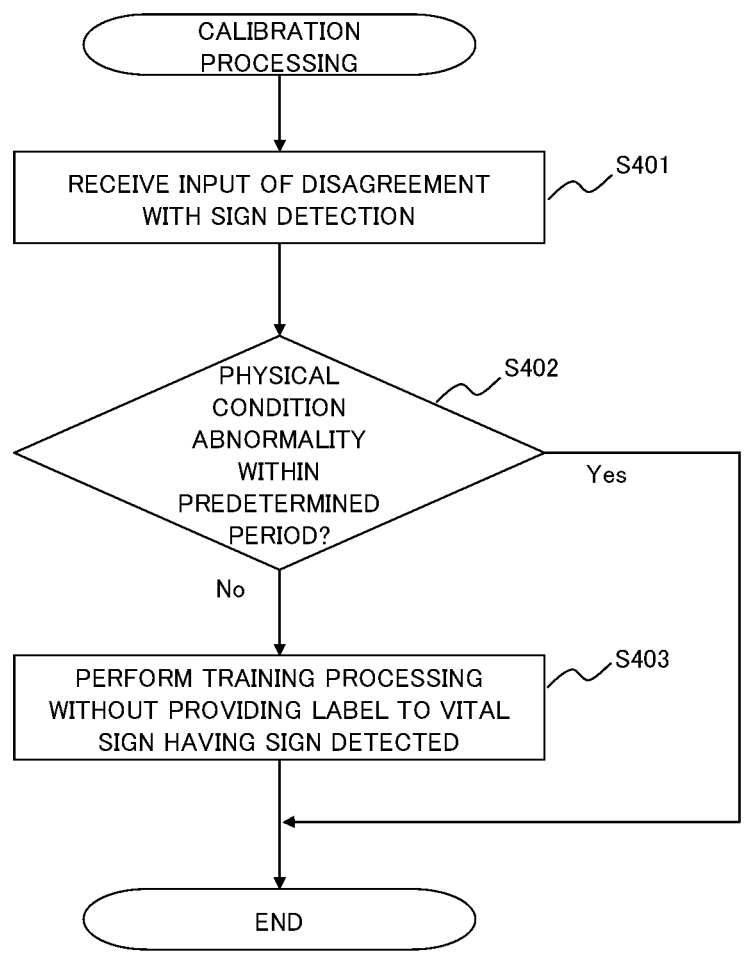
FIG. 13 is a diagram illustrating an example of a flow of calibration processing.

FIG. 13 is a diagram illustrating an example of a flow of calibration processing. The calibration processing starts when it is determined as "Yes" in step S004.

First, the training data generation unit 118 receives an input of a disagreement with sign detection (step S401). Specifically, in a case of the arousal abnormality notification screen 600 output in step S005 in the sign detection processing, the training data generation unit 118 receives a touch input to the region in which an input of a disagreement, such as "Not sleepy", is received.

Then, the training data generation unit 118 determines whether or not a physical condition abnormality occurs within a predetermined period (step S402). Specifically, the training data generation unit 118 receives the input of the disagreement in step S401, and then starts measuring a predetermined period. Then, during the measurement, the training data generation unit 118 monitors whether or not a predetermined signal according to the physical condition abnormality is output in the physical condition abnormality detection processing.

When the physical condition abnormality occurs within the predetermined period (in a case of "Yes" in step S402), the training data generation unit 118 terminates the calibration processing. The reason is that the disagreement is not correct, it is a situation where a symptom of the physical condition abnormality needs to be detected, and a sign model does not need to be changed.

When the physical condition abnormality does not occur within the predetermined period (in a case of "No" in step S402), the training data generation unit 118 changes the vital sign having the sign detected to training data without being provided with a label, and generates the training data (step S403). The reason is that the disagreement is correct, it is not a situation where a symptom of the physical condition abnormality needs to be detected, and a sign model needs to be adjusted according to individuality.

The example of the flow of the calibration processing is described above. According to the calibration processing, it is possible to calibrate a model to be suitable for a user, to individualize, from a general-purpose model, a sign model handling a vital sign having an individual difference due to a predisposition and the like for each user, and to increase accuracy of detecting a sign.

The state extrapolation device 100 to which the embodiment according to the present invention is applied is described above. According to the state extrapolation device 100, it is possible to more appropriately extrapolate a sign of a state that may affect a movement of a user.

However, the present invention is not limited to the embodiment described above. In the embodiment described above, various modifications can be made within a range of a technical scope of the present invention. For example, in the embodiment described above, the sign detection processing, the physical condition abnormality detection processing, the training data generation processing, the training processing, the model updating processing, and the calibration processing are performed, which is not limited thereto. Any of the processing may be performed alone or in combination.

Figure 14:
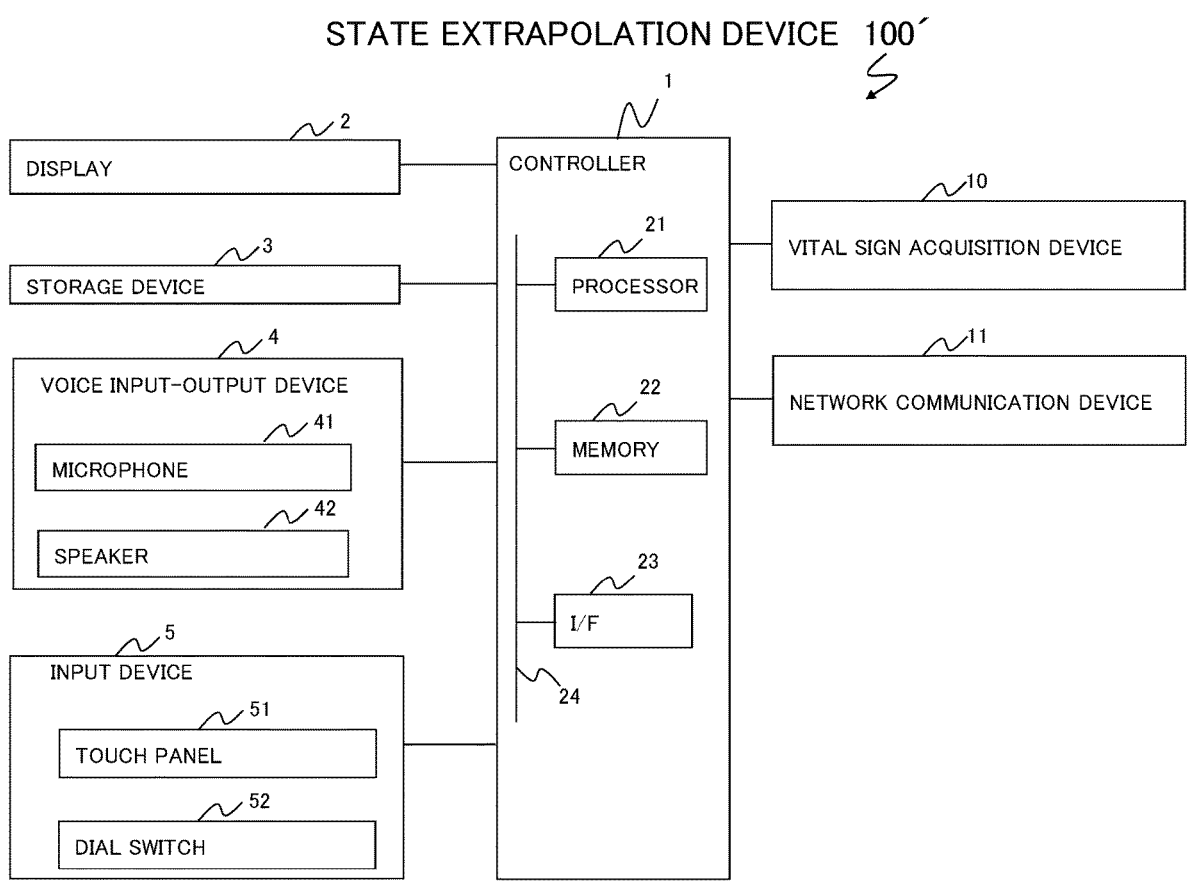
FIG. 14 is a diagram illustrating an example of a structure of a state extrapolation device to which a second embodiment is applied.

FIG. 14 is a diagram illustrating an example of a structure of a state extrapolation device to which a second embodiment is applied. A state extrapolation device 100' to which the second embodiment is applied is basically similar to, but partially different from the state extrapolation device 100 to which the embodiment described above is applied. The difference will be mainly described.

The state extrapolation device 100' to which the second embodiment is applied does not include the state detection device 12. Accordingly, the storage device 3 does not include the training data storage unit 400 and the training data learning ratio-storage unit 500. Then, the controller 1 performs the sign detection processing, but does not perform the physical condition abnormality detection processing, the training data generation processing, the training processing, the model updating processing, and the calibration processing.

In other words, a sign is detected from a vital sign acquired by using a learned sign model without performing relearning by performance data of a sign model. In this way, a sign of a state that may affect a movement of a user can be appropriately extrapolated while suppressing various costs such as a hardware cost and a software cost.

Figure 15:
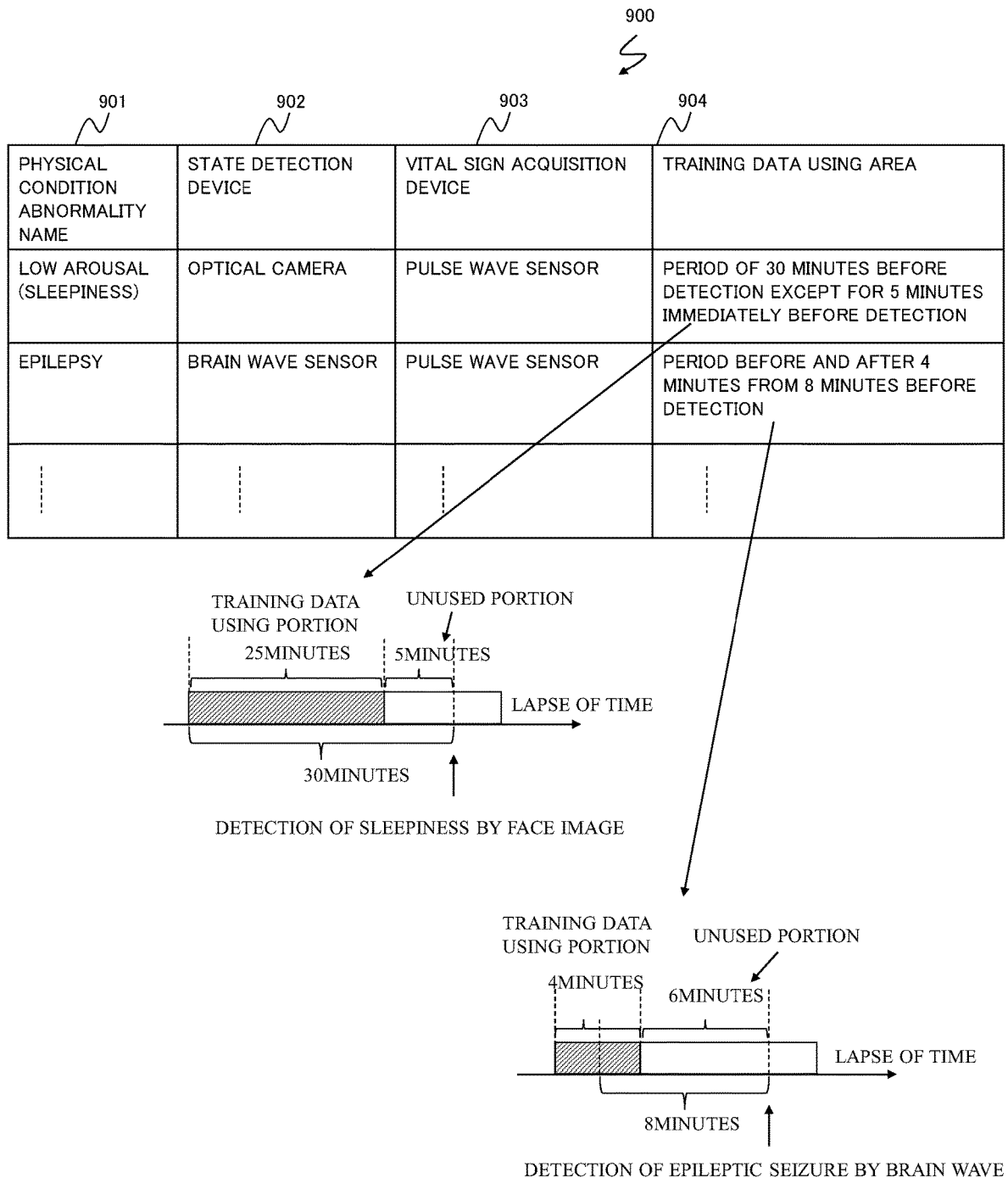
FIG. 15 is a flowchart illustrating an example of training data setting information according to a third embodiment.

FIG. 15 is a flowchart illustrating an example of training data setting information according to a third embodiment. A state extrapolation device to which the third embodiment is applied more accurately detects a state and accurately generates training data and a sign model in order to achieve sign detection with higher accuracy being simultaneously performed on a plurality of physical condition abnormalities.

Training data setting information 900 is information that individually sets, for each physical condition abnormality name 901, a state detection device 902, a vital sign acquisition device 903, and a training data using area 904 to be used, in order to achieve such a purpose. The training data using area 904 is specifically a period specified with reference to a physical condition abnormality detection point and a point going back over a predetermined period from the physical condition abnormality detection point. For example, for low arousal (sleepiness), the training data using area 904 is a "period of 30 minutes before detection except for 5 minutes immediately before detection", and for epilepsy, the training data using area 904 is a "period before and after 4 minutes from 8 minutes before detection". The training data setting information 900 is stored in the storage device 3. The state detection unit 117 of the controller 1 refers to the state detection device 902, and identifies a state detection device to be used for each physical condition abnormality. The vital sign acquisition unit 114 refers to the vital sign acquisition device 903, and identifies a vital sign acquisition device to be used for each physical condition abnormality.

Then, the sign detection unit 115 operates, in parallel, one or a plurality of sign models according to an acquired vital sign, and detects a sign by using a plurality of learned models that each have learned a plurality of physical condition abnormalities. In this way, optimum sign detection can be achieved according to each physical condition abnormality, and sign detection can be performed with higher accuracy.

The training data generation unit 118 refers to the training data using area 904, and specifies an area of a vital sign to be used for each physical condition abnormality. In this way, information more suitable for a physical condition abnormality can be used simultaneously for a plurality of physical condition abnormalities, and sign detection can be performed with higher accuracy.

In each of the embodiments described above, when a signal of a physical condition abnormality is not detected, a label provided to training data is handled to be absent, which is not limited thereto. A label that does not indicate a physical condition abnormality may be provided. For example, for the label 402 described above, when a vital sign does not indicate a sign of a predetermined physical condition abnormality, in other words, since this case is also conceivable that a vital sign is a normal vital sign without a physical condition abnormality, a dummy variable may be set to the label 402. Specifically, the dummy variable represents two states by "0" and "1". When a vital sign indicates a sign of a physical condition abnormality, the dummy variable "1" may be used, and otherwise, the dummy variable "0" may be used.

When the dummy variable is used as the label 402 in such a manner, for example, in the case of "Yes" in step S402 in the calibration processing (when a physical condition abnormality occurs within a predetermined period), the training data generation unit 118 provides the dummy variable "1" as the label 402 and terminates the calibration processing.

In the case of "No" in step S402 in the calibration processing (when a physical condition abnormality does not occur within the predetermined period), the training data generation unit 118 changes a vital sign having a sign detected to training data having a label provided with the dummy variable "0", and generates the training data in step S403.

In this way, even when a physical condition abnormality does not occur, by providing label data indicating this point to training data, an unexpected learning result due to a lack of the label data can be avoided.

What is claimed is:

1. A state extrapolation device comprising:
a vital sign acquisition unit that acquires a vital sign of a user;
a sign detection unit that uses a learned model that has learned, as training data, sign data about the vital sign related to a predetermined physical condition abnormality, and detects a sign by determining whether or not the vital sign of the user corresponds to a sign of the predetermined physical condition abnormality;
a training data generation unit that generates the training data as the training data including a vital sign of the user;
a sign model generation unit that causes the learned model to learn the training data generated by the training data generation unit; and
a state detection unit that detects an occurrence state of the predetermined physical condition abnormality of the user, wherein
the training data generation unit generates, when the state detection unit detects the occurrence state, the training data by using first information being the vital sign of the user provided with a label in a predetermined period before the occurrence state, and second information being the vital sign of the user in the predetermined period when the occurrence state is not detected.

2. The state extrapolation device according to claim 1, wherein
the predetermined physical condition abnormality is a physical condition abnormality that affects an exercise movement of the user.

3. The state extrapolation device according to claim 2, wherein
the physical condition abnormality that affects the exercise movement of the user is a state where the user feels sleepiness or a state where the user has an epileptic seizure.

4. The state extrapolation device according to claim 1, wherein
the vital sign acquisition unit acquires information about a pulse wave as the vital sign.

5. The state extrapolation device according to claim 1, wherein
the training data generation unit generates the training data so as to set the first information and the second information at a predetermined ratio.

6. The state extrapolation device according to claim 1, wherein
the training data generation unit specifies the predetermined period according to the physical condition abnormality.

7. The state extrapolation device according to claim 1, wherein,
when the training data generation unit receives an input indicating a disagreement with a sign detected by the sign detection unit, in a case where the state detection unit does not subsequently detect the occurrence state within a predetermined period, the training data generation unit generates training data in which a vital sign having the sign detected is set to second information.

8. The state extrapolation device according to claim 1, further comprising
a notification unit that notifies an abnormality by a predetermined method, wherein
the vital sign acquisition unit causes the notification unit to make a notification when the acquired vital sign deviates from a predetermined range, and deletes the vital sign.

9. The state extrapolation device according to claim 1, wherein
the sign detection unit detects a sign of a plurality of the predetermined physical condition abnormalities by using a plurality of learned models that each have learned the plurality of predetermined physical condition abnormalities.

10. A product comprising programs stored in a non-transitory computer readable medium causing a computer to execute a state extrapolation procedure, the program causing the computer to function as a control means, and
    causing the control means to perform:
        a vital sign acquisition step of acquiring a vital sign of a user;
        a sign detection step of using a learned model that has learned, as training data, sign data about the vital sign related to a predetermined physical condition abnormality, and detecting a sign by determining whether or not the vital sign of the user corresponds to a sign of the predetermined physical condition abnormality;
    a training data generation step that generates the training data as the training data including a vital sign of the user;
    a sign model generation step that causes the learned model to learn the training data generated by the training data generation unit; and
    a state detection step that detects an occurrence state of the predetermined physical condition abnormality of the user, wherein
    the training data generation step generates, when the state detection step detects the occurrence state, the training data by using first information being the vital sign of the user provided with a label in a predetermined period before the occurrence state, and second information being the vital sign of the user in the predetermined period when the occurrence state is not detected.

11. A state extrapolation method causing a computer to execute a state extrapolation procedure, the computer including a control means, the state extrapolation method comprising:
    by the control means,
    a vital sign acquisition step of acquiring a vital sign of a user;
    a sign detection step of using a learned model that has learned, as training data, sign data about the vital sign related to a predetermined physical condition abnormality, and detecting a sign by determining whether or not the vital sign of the user corresponds to a sign of the predetermined physical condition abnormality;
    a training data generation step that generates the training data as the training data including a vital sign of the user;
    a sign model generation step that causes the learned model to learn the training data generated by the training data generation unit; and
    a state detection step that detects an occurrence state of the predetermined physical condition abnormality of the user, wherein
    the training data generation step generates, when the state detection step detects the occurrence state, the training data by using first information being the vital sign of the user provided with a label in a predetermined period before the occurrence state, and second information being the vital sign of the user in the predetermined period when the occurrence state is not detected.

* * * * *